United States Patent
Werning et al.

(10) Patent No.: US 12,216,141 B2
(45) Date of Patent: Feb. 4, 2025

(54) PULL TAB WITH CONDUCTIVE PADS

(71) Applicant: TERUMO KABUSHIKI KAISHA, Tokyo (JP)

(72) Inventors: Julia Werning, Redwood City, CA (US); Yuichi Tada, Santa Clara, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 301 days.

(21) Appl. No.: 17/548,265

(22) Filed: Dec. 10, 2021

(65) Prior Publication Data

US 2022/0187340 A1  Jun. 16, 2022

Related U.S. Application Data

(60) Provisional application No. 63/124,580, filed on Dec. 11, 2020.

(51) Int. Cl.
| | |
|---|---|
| *G01R 1/20* | (2006.01) |
| *A61B 17/00* | (2006.01) |
| *G01R 31/385* | (2019.01) |
| *G01R 31/56* | (2020.01) |
| *H01M 50/598* | (2021.01) |
| *A61B 17/32* | (2006.01) |
| *H01H 27/04* | (2006.01) |

(52) U.S. Cl.
CPC ............ *G01R 1/20* (2013.01); *G01R 31/385* (2019.01); *G01R 31/56* (2020.01); *H01M 50/598* (2021.01); *A61B 2017/00734* (2013.01); *A61B 17/320016* (2013.01); *H01H 27/04* (2013.01); *H01H 2239/062* (2013.01)

(58) Field of Classification Search
CPC ........ G01R 31/56; G01R 1/20; G01R 31/385; H01M 50/598; A61B 17/320016; A61B 2017/00734; H01H 27/04; H01H 2239/062
USPC ............................... 324/92, 500, 600, 76.11
See application file for complete search history.

(56) References Cited

U.S. PATENT DOCUMENTS

| | | | | |
|---|---|---|---|---|
| 2008/0278336 | A1* | 11/2008 | Ortega | A61B 5/002 340/573.5 |
| 2012/0179234 | A1* | 7/2012 | Carrington | A61N 1/046 607/142 |
| 2019/0022388 | A1* | 1/2019 | Stucke | A61N 1/36031 |
| 2020/0174082 | A1* | 6/2020 | Wu | H01M 10/0436 |
| 2022/0365122 | A1* | 11/2022 | Kim | G01R 27/025 |
| 2024/0110990 | A1* | 4/2024 | Lee | G01R 31/389 |

\* cited by examiner

*Primary Examiner* — Huy Q Phan
*Assistant Examiner* — Trung Q Nguyen
(74) *Attorney, Agent, or Firm* — Kim & Stewart LLP

(57) ABSTRACT

An insulating tab attached to an electronic device driven by a battery includes a first insulating layer, a first wiring that extends in a first direction along the first insulating layer, the first wiring including a first electrode on one end thereof and a second electrode on the other end thereof, and a second wiring that extends in the first direction along the first insulating layer, the second wiring including a third electrode on one end thereof and a fourth electrode on the other end thereof. The first and third electrodes are disposed on opposite sides of the first insulating layer at a first location of the first insulating layer along the first direction.

21 Claims, 12 Drawing Sheets

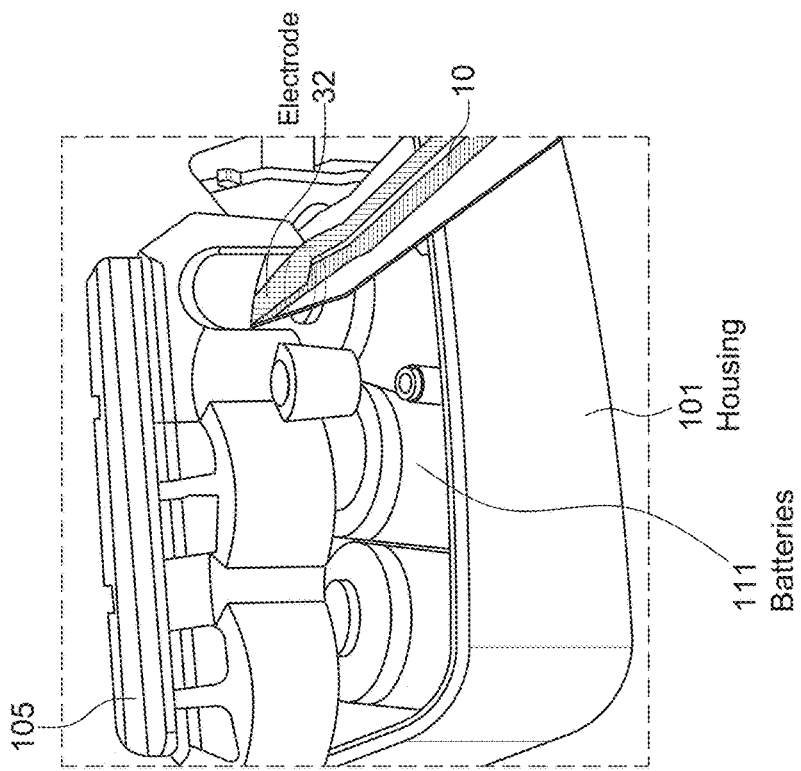
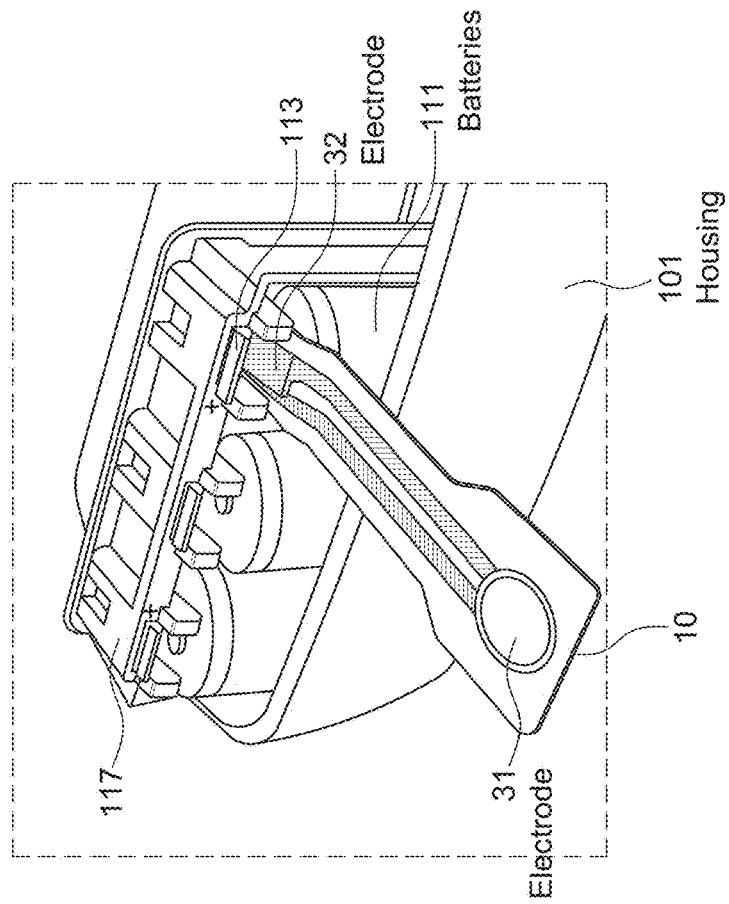
FIG. 5
FIG. 4

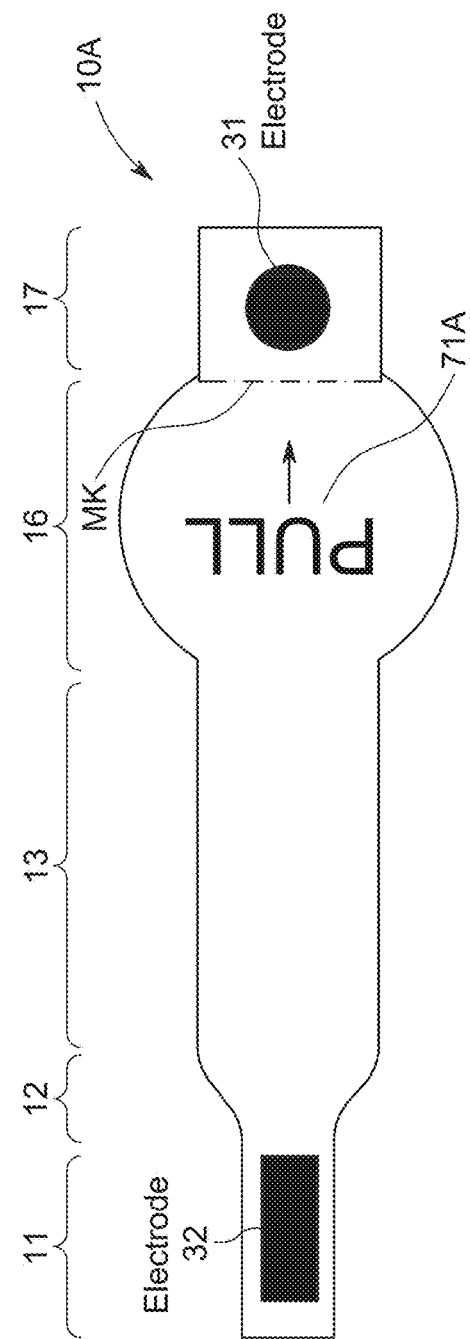
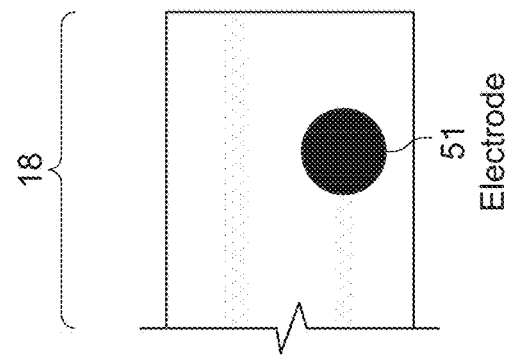
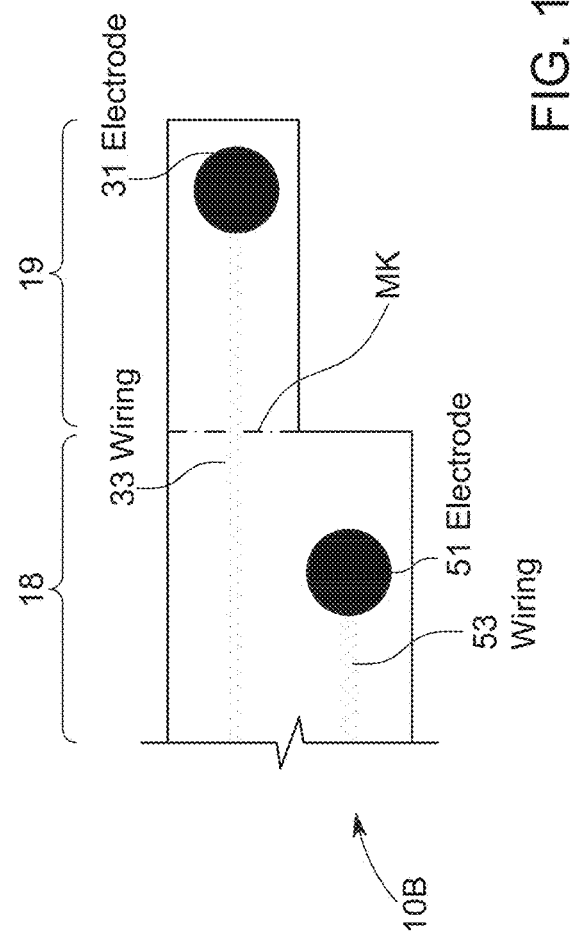
FIG. 11
FIG. 12

PULL TAB WITH CONDUCTIVE PADS

CROSS REFERENCE TO RELATED APPLICATIONS

This patent application claims priority to U.S. Provisional Patent Application No. 63/124,580, titled "PULL TAB WITH CONDUCTIVE PADS" and filed on Dec. 11, 2020. This application is herein incorporated by reference in its entirety.

TECHNICAL FIELD

Embodiments of the present disclosure relate to an insulating tab attached to an electronic device, an electronic device having such an insulating tab, and an inspection method of the electronic device.

BACKGROUND

A battery insulating pull tab or a battery insulator is widely used to keep a battery embedded in an electronic device insulated from the other electrical components until the end user receives the device and starts using it after removing the tab. Such an electrical device is typically configured to perform a self-test upon its initial start-up to inspect the functions of the electrical components and the condition of the battery.

In some industries such as the healthcare industry, a device shipped from its manufacturer is received by an intervening party, e.g., a local distributer, who is responsible for inspection including the execution of the self-test before the device is delivered to the end user. Because the insulating tab needs to remain in place until the actual use of the device begins, some extra work, such as providing external power and disassembling the device, needs to be done by the intervening party to run the self-test. Such extra work burdens the intervening party, and thus there is a need for a solution that facilitates the inspection of a battery-powered device with an insulating tab.

SUMMARY OF THE INVENTION

In an embodiment, an insulating tab attached to an electronic device driven by a battery includes a first insulating layer, a first wiring that extends in a first direction along the first insulating layer, the first wiring including a first electrode on one end thereof and a second electrode on the other end thereof, and a second wiring that extends in the first direction along the first insulating layer, the second wiring including a third electrode on one end thereof and a fourth electrode on the other end thereof. The first and third electrodes are disposed on opposite sides of the first insulating layer at a first location of the first insulating layer along the first direction.

BRIEF DESCRIPTION OF THE DRAWINGS

FIGS. 4 and 5 depict a battery holder of a medical device according to one embodiment.

FIGS. 11 through 15 depict insulating tabs according to various embodiments.

DESCRIPTION OF EMBODIMENTS

The following detailed description describes a medical device as an example of an electronic device to which a battery insulating pull tab is attached. Various embodiments of such a medical device and an insulating tab are described with reference drawings.

Figure 1:
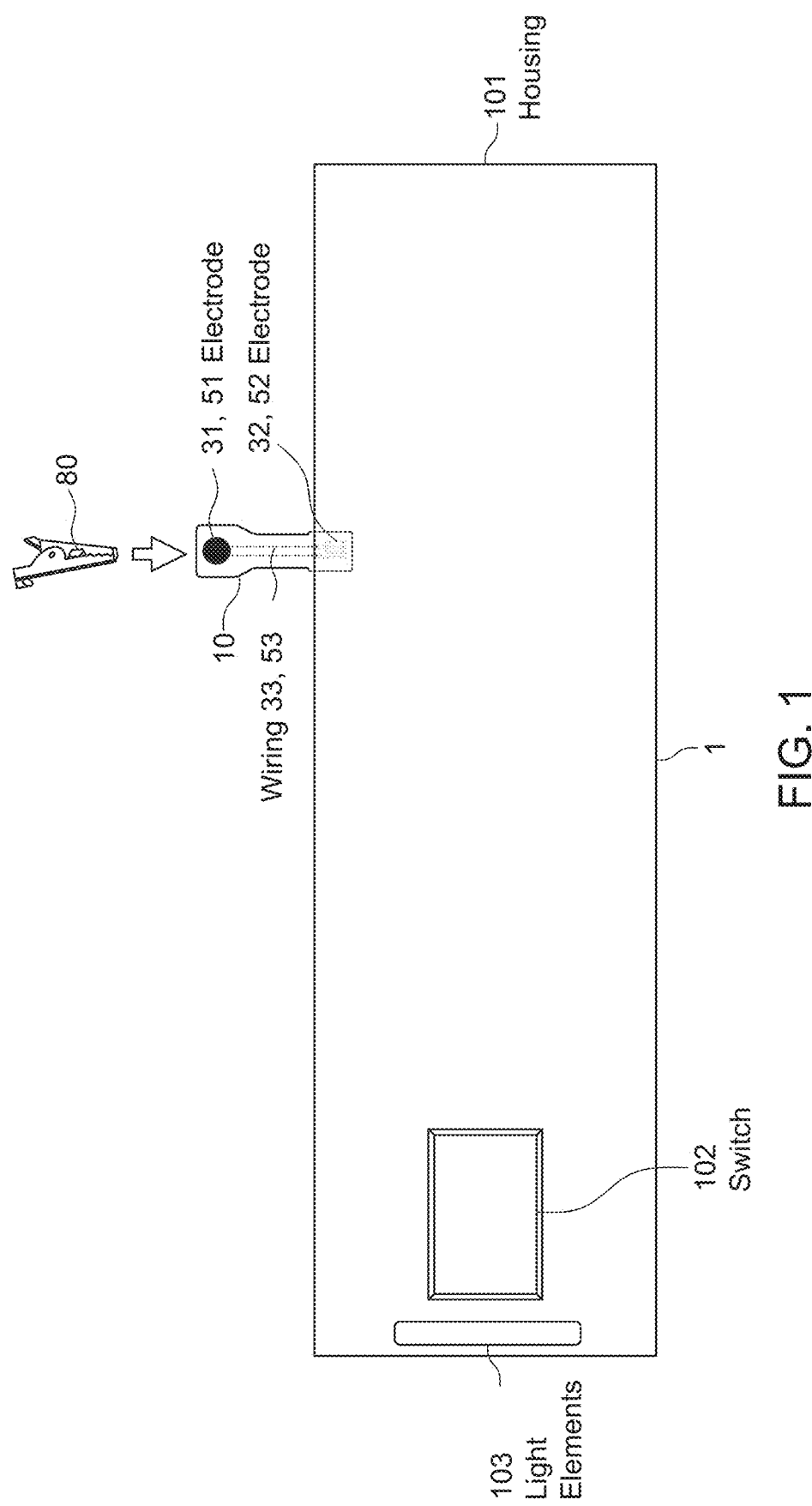
FIGS. 1 and 2 depict a medical device to which a detachable insulating tab is attached according to one embodiment.
Figure 2:
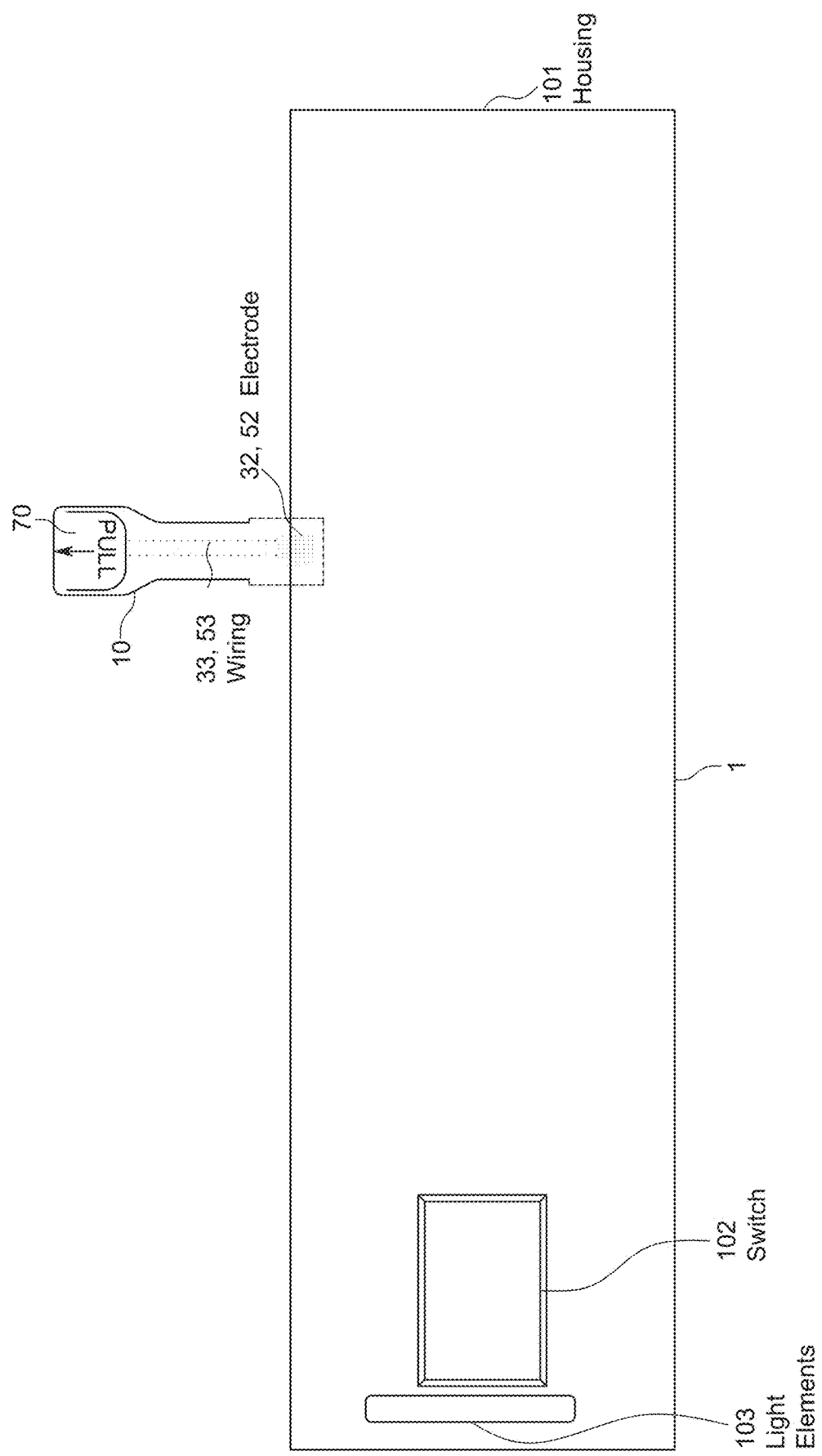

FIGS. 1 and 2 depict a medical device 1 to which a battery insulating tab 10 is attached according to one embodiment. The medical device 1 is a battery-drive, motorized catheter. For example, the medical device 1 aspirates objects that have been removed from a body lumen via a catheter inserted thereto. The catheter is connected to an end of the medical device 1 via a connector mechanism. The medical device 1 has a pump and a motor to drive the pump to aspirate those objects and discharge them to a collection bag connected to the other end of the medical device 1.

The medical device 1 is battery driven, and has an embedded battery in a housing 101. As shown in FIGS. 1 and 2, the insulating tab 10 is attached as a temporary insulator between the battery and the internal electrical circuit of the medical device 1 until the end user starts the use of the medical device 1.

In one embodiment, the insulating tab 10 has two electrodes 31 and 32 connected to each other via a wiring 33 on one side of the insulating tab 10, and two electrodes 51 and 52 connected to each other via a wiring 53 on the other side of the insulating tab 10. The electrodes 31 and 32 and the writing 33 are insulated from the electrodes 51 and 52 and the wiring 53 by an insulating layer. The wirings 33 and 53 are embedded in the insulating tab 10 and thus are invisible, whereas the electrodes 31, 32, 51, and 52 are exposed from the surfaces of the insulating tab 10.

The electrodes 32 and 52 face the opposite directions inside the housing 101. In one embodiment, the electrodes 32 and 52 are located between a terminal of the battery and an electrode for electrically connecting the battery terminal to the internal electrical circuit. In other words, the circuit is made incomplete by the insulated electrodes 32 and 52 inside the housing 101.

The electrodes 31 and 51 are located outside the housing 101 so that a conductive clip 80 made of a conductive material can be attached thereon. The circuit is made complete by the conductive clip 80, and the medical device 1 can operate using battery power until the conductive clip 80 is removed. Any conductive material such as a metal clip can be used for the conductive clip 80. With this configuration, an intervening party of the medical device such as a local distributor, can inspect the medical device 1 by running a test such as a self-test and an actual functional test (e.g., turning on and off a switch) prior to the delivery to the end user without removing the insulating tab 10.

In one embodiment, the medical device 1 includes a switch 102 and one or more light elements 103. The switch 102 is a power switch to turn on and off the medical device 1. For example, the medical device 1 is configured to perform a self-test upon initial boot after the shipment from the manufacturer. The self-test checks whether electrical components of the medical device 1 are working properly and also checks the condition of the battery. The light elements 103 emit light of different colors depending on the result of the self-test. With this configuration, the intervening party can determine whether to ship the medical device 1 or discard it because of some defect.

In one embodiment, after the self-test is successfully done, a non-transparent, non-conductive sticker 70 is attached to the end of the insulating tab 10 to cover the electrodes 31 and 51, as shown in FIG. 2. As a result, the electrodes 31 and 51 become invisible to the end user, which allows him or her to treat the insulating tab 10 as a conventional insulating pull tab.

Figure 3:
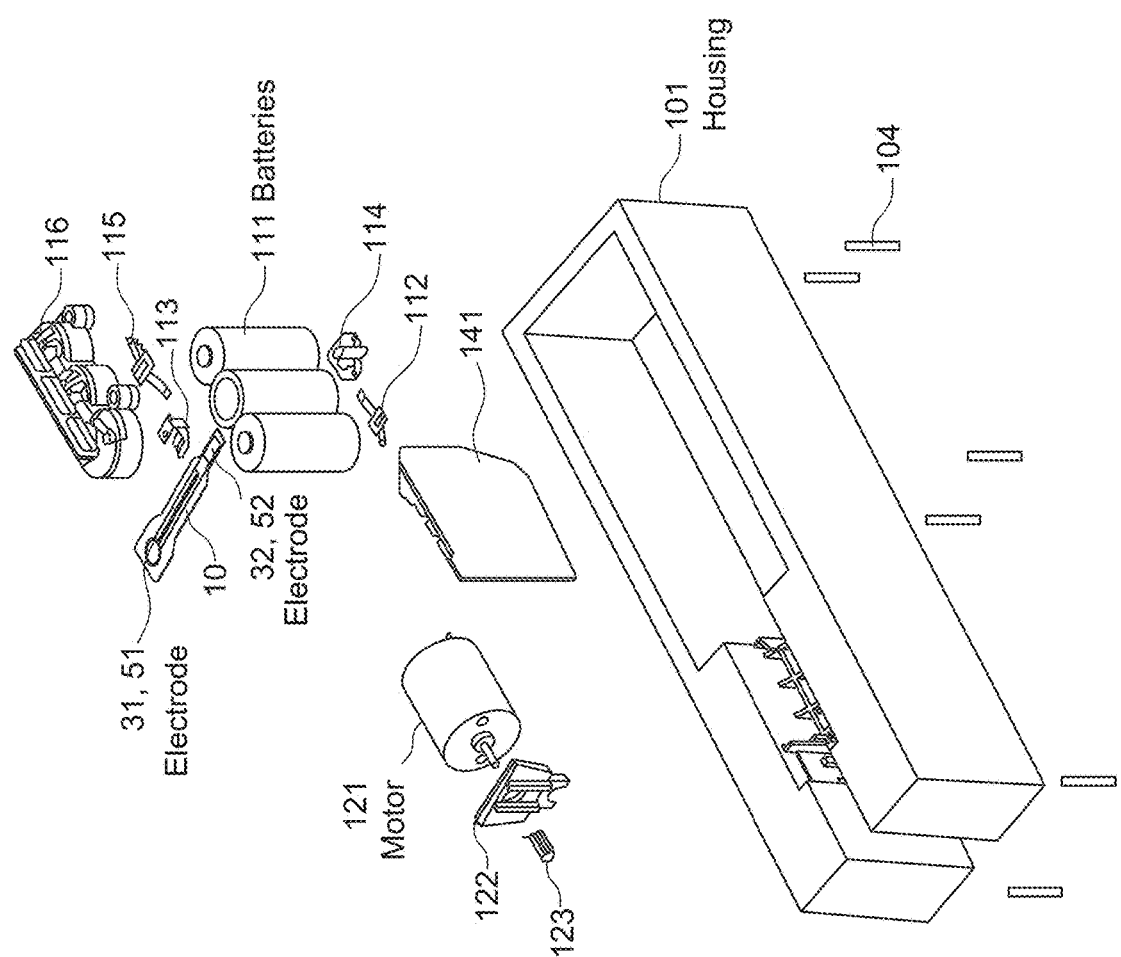
FIG. 3 depicts an internal structure of a medical device according to one embodiment.

FIG. 3 depicts an internal structure of the medical device 1 according to one embodiment. Some of the components of the medical device 1 including internal wirings that are not illustrated in FIG. 3 for simplification. The medical device 1 includes a plurality of screws 104 for fixing a cover (not shown) to the housing 101. The medical device 1 further includes one or more batteries 111, a plurality of electrodes 112-115 each contacting a terminal of the batteries 111 or the electrode 32 or 52 of the insulating tab 10, and a holding member 116 for holding the batteries 111. The battery power is supplied to, via one or more wirings, an electrical circuit 141 configured to control the other components of the medical device 1 to perform the functions thereof including the self-test. In one embodiment, the insulating tab 10 is inserted between the electrode 113 and a terminal of one of the batteries 111. In other words, the electrodes 32 and 52 respectively contact the electrode 113 and the terminal of one of the batteries 111 so that there is an interruption in the circuit to prevent current flow. This is a safety measure for sterilization and shipping and additionally preserves the shelf life of the medical device 1.

The medical device 1 further includes a motor 121 that drives a blade in the catheter, a motor cover plate 122, a gear 123 for transmitting mechanical rotation to the catheter, an aspiration pump (not shown) to aspirate debris, an aspiration tube (not shown) through which debris that has been removed from a body lumen is transferred, and a connector (not shown) to which a catheter or a connector mechanism thereof is connected.

FIGS. 4 and 5 depict different types of battery holders 117 for holding the batteries 111 inside the housing 101. In the example of FIG. 4, the battery holder 117 is attached to the housing 101 after the batteries 111 are set therein. The insulating tab 10 is inserted between the electrode 113 and the terminal of one of the batteries 111 as described above and protrudes towards the outside of the housing 101. In the example of FIG. 5, a part of the housing 101 forms the battery holder 117, and a battery holder cover 105 is attached to the housing 101 by one of the screws 104 to hold the batteries 111. The cover 105 has an opening near the electrode 113 so that the side wall of the cover 105 does not interfere the insulating tab 10 extending towards the outside of the housing 101.

Figure 6:
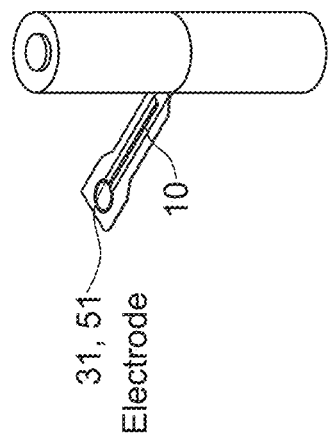
FIG. 6 depicts an arrangement of an insulating tab and batteries according to one embodiment.

FIG. 6 depicts an arrangement of the insulating tab 10 and the batteries 111, which is different from the arrangement shown in FIGS. 3-5. Here, the battery holder 117 and the electrodes 112-115 are not illustrated. In one embodiment, the insulating tab 10 (i.e., the electrodes 32 and 52) is inserted between the terminals of two batteries that are connected in series. The insulating tab 10 may be inserted between any conductive components of the medical device 1 as long as there is interruption of the circuit including the batteries 111.

Figure 7:
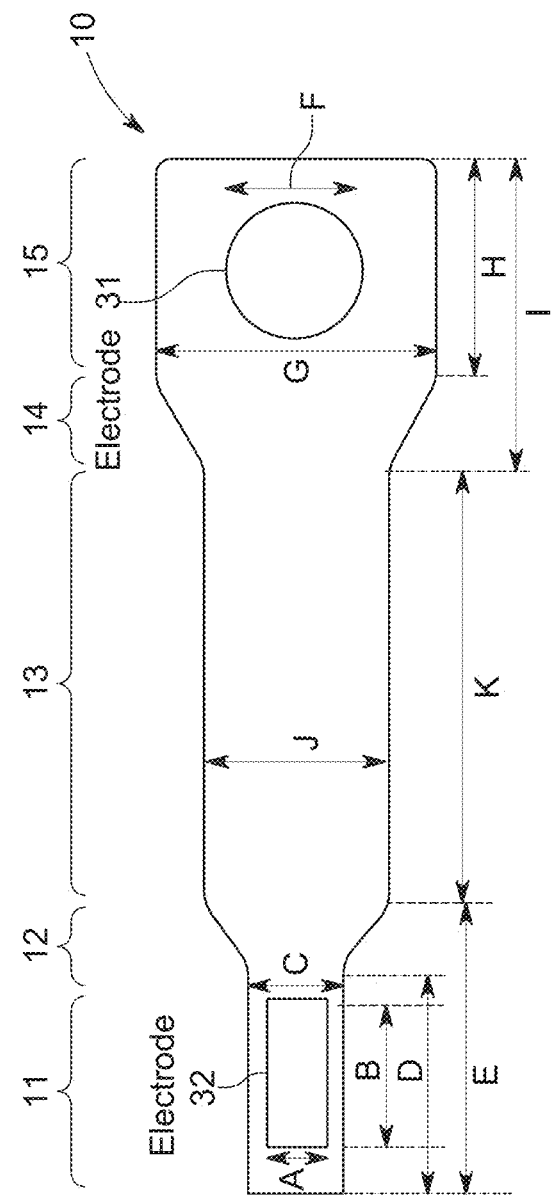
FIGS. 7 through 9 depict an insulating tab according to one embodiment.
Figure 8A:
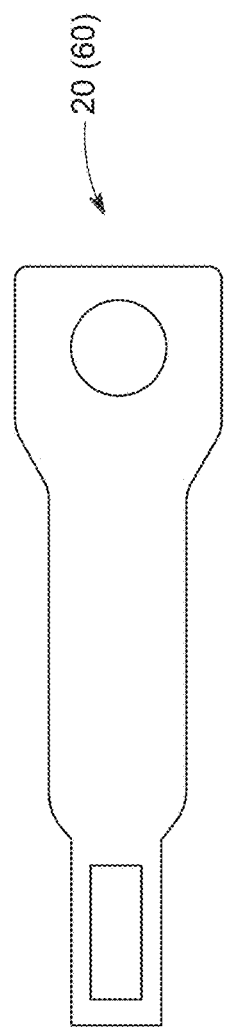
Figure 8B:
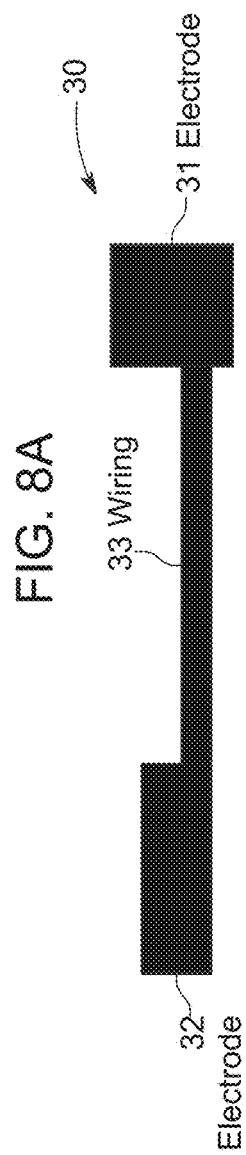
Figure 8C:
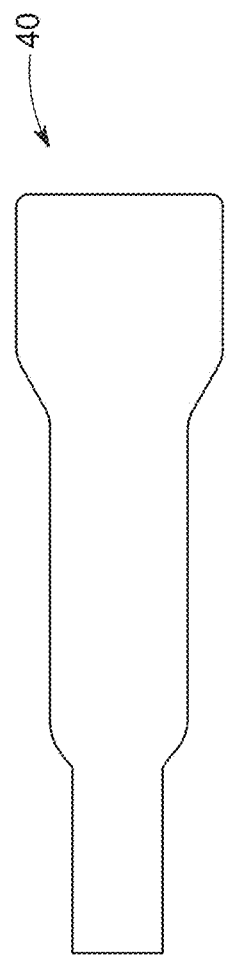
Figure 8D:
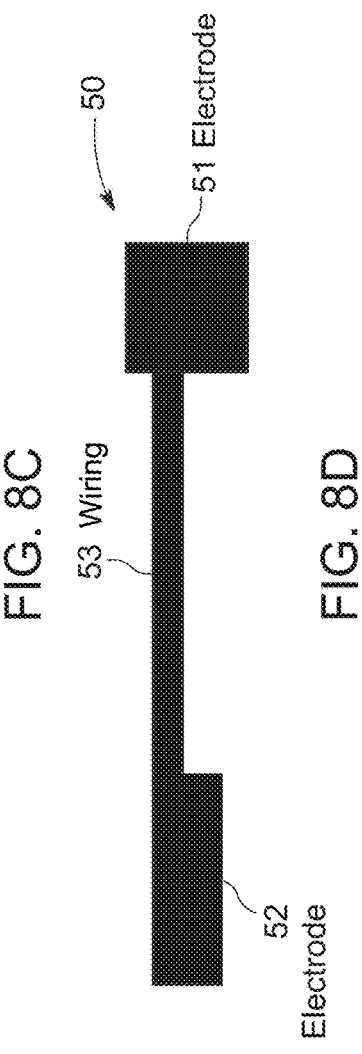
Figure 9:
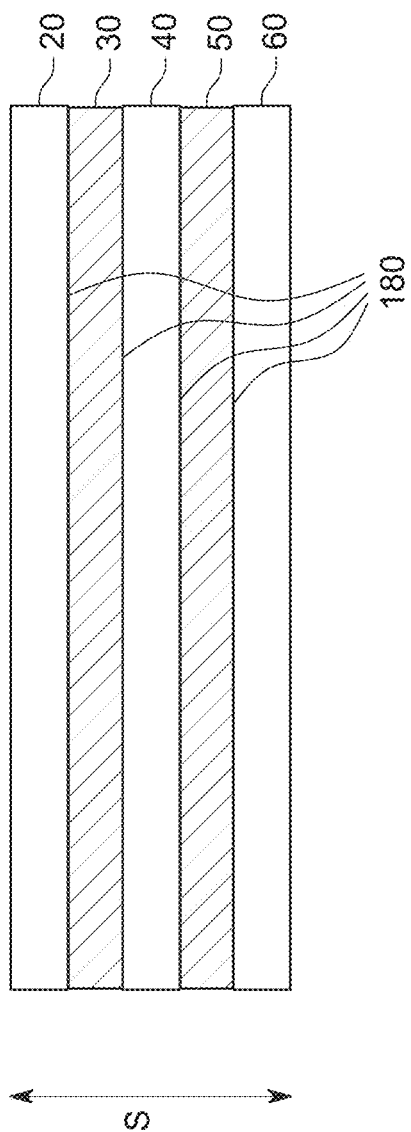

FIGS. 7 through 9 depict the details of the insulating tab 10. In one embodiment, the insulating tab 10 includes five layers 20-60 and a plurality of adhesive layers 180. FIG. 7 shows a plan view of the insulating tab 10, which illustrates the electrodes 31 and 32 and the upper most layer 20 that are visible from above. FIGS. 8A through 8D illustrate the upper and lower cover layers 20 and 60, the conductive layer 30 including the electrodes 31 and 32 and a wiring 33 therebetween, the insulating base layer 40, and the conductive layer 50 including the electrodes 51 and 52 and a writing 53 therebetween. As shown in FIG. 9, those layers 20-60 are stacked and adhere to each other by the adhesive layers 180. The stacked structure has a thickness S of about 0.25 mm so as to be flexible. The cover layers 20 and 60 and the base layer 40 are made of an insulating material, such as polyethylene terephthalate (PET). Any other insulating material may be used for those layers 20, 40, and 60. The conductive layers 30 and 50 are made of a conductive material, such as copper. Any other conductive material, e.g., copper alloys and aluminum, may be used for the conductive layers 30 and 50.

As shown in FIG. 7, the electrode 32, which is a part of the conductive layer 30, is exposed from an opening of the upper cover layer 20, and the electrode 31, which is another part of the conductive layer 30, is exposed from another opening of the upper cover layer 20. Similarly, the electrode 52, which is a part of the conductive layer 50, is exposed from an opening of the lower cover layer 60, and the electrode 51, which is another part of the conductive layer 50, is exposed from another opening of the lower cover layer 60.

In one embodiment, the opening for each of the electrodes 32 and 52 has a rectangular shape, which has a width A of about 4 mm and a length B of about 8 mm. Each opening may have any shape having any dimension as long as the exposed electrode 32 and 52 fits the battery holder 117 of the medical device 1.

In one embodiment, the opening for each of the electrodes 31 and 51 has a circle shape, which has a diameter F of about 7 mm. The opening may have any shape having any dimension.

In one embodiment, a width C of a portion 11 of the insulating tab 10 at which the electrodes 32 and 52 are located (hereinafter referred to as "narrow portion 11") is about 5 mm. A width J of a portion 13 of the insulating tab 10 at which none of the electrodes 32, 52, 31, and 51 is located (hereinafter referred to as the "central portion 13") is about 10 mm. A width G of a portion 15 of the insulating tab 10 at which the electrodes 31 and 51 are located (hereinafter referred to as the "wide portion 15") is about 15 mm. As shown in FIG. 7, the width gradually changes at a portion 12 between the narrow portion 11 and the central portion 13 (hereinafter referred to as the "connecting portion 12") and a portion 14 between the central portion 13 and the wide portion 15 ("hereinafter referred as the "connecting portion 14").

In one embodiment, the narrow portion 11 has a length D of about 12 mm. The distance E from the edge of the narrow portion 11 to one end of the central portion 13 is about 15 mm. The central portion 13 has a length K of about 25 mm. The distance H of the wide portion 15 is about 12 mm, and the distance I from the edge of the wide portion 15 to the other end of the central portion 13 is about 16 mm.

As shown in FIG. 7, the width of the insulating tab 10 is smaller at one end thereof at which the electrodes 32 and 52 are located than the other end thereof. As described above, the electrodes 32 and 52 are inserted into the battery holder 117 of the medical device 1. Thus, a part of the insulating tab 10 having less contact with the batteries 111 and/or the electrode 113 enables smooth removal when the actual use of the medical device 1 by the end user begins. The smaller width at one end of the insulating tab 10 also provides a feature for placement during assembly. The assembler can insert the tab into the battery holder 117 until the interference between the widening of the insulating tab 10 and the battery holder 117 stops the insertion. This design ensures the electrodes 32 and 52 are accurately positioned.

Figure 10:
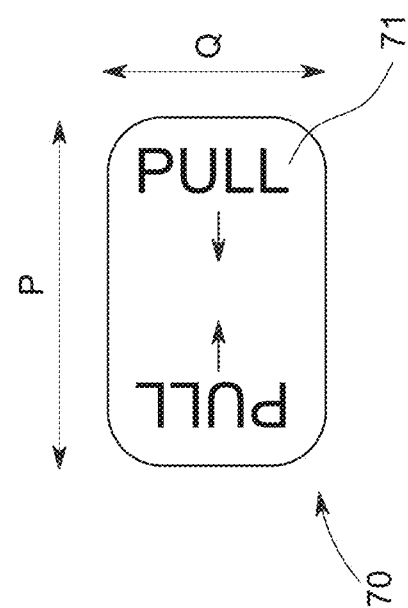
FIG. 10 depicts a sticker for covering electrodes of an insulating tab according to one embodiment.

FIG. 10 depicts the sticker 70 for covering the electrodes 31 and 51. As described above, the sticker 70 is made of an insulating material such as paper or plastic material and having a surface to which an adhesive is applied. A print 71 is printed on the outer surface, indicating the direction towards which the insulating tab 10 should be pulled. The print 71 may or may not include one or more characters and/or images for indicating how to remove the insulating tab 10. The sticker 70 is nontransparent so that the electrodes 31 and 51 to be covered thereby are not visible. In one embodiment, the sticker 70 has a length P of about 22 mm and a width Q of about 12 mm. The sticker 70 may have any length and width as long as it can cover both the electrodes 31 and 51.

According the above-described embodiments, the medical device 1 can be inspected using its own battery power with the insulating tab 10 attached thereto. The medical device 1 can perform the self-test when the electrodes 31 and 51 of the insulating tab 10 located outside the housing 101 are electrically connected. When the self-test is successfully done, the medical device 1 can be delivered to the end user with the sticker 70 attached to the insulating tab 10. Since the sticker 70 covers the electrodes 31 and 51, the end user treats the insulating tab 10 as a conventional battery insulating pull tab and removes the insulating tab 10 before beginning the actual use of the medical device 1.

FIG. 11 depicts an insulating tab 10A according to an embodiment. Unlike the insulating tab 10 shown in FIG. 7, the insulating tab 10A has a holding portion 16 adjacent to the electrodes 31 and 51, which is wider than the other portions of the insulating tab 10A. Additionally, one or more of the layers 20-60 have markings MK such as dashed markings between the holding portion 16 and the electrodes 31 and 51 such that a portion 17 of the insulating tab 10 including the electrodes 31 and 51 may be cut off. Further, one or more of the layers 20-60 may have perforated cut lines along the markings MK so that the portion 17 of the insulating tab 10 can be easily detached. The holding portion 16 and the portion 17 may have any shape having any dimension. In the example of FIG. 11, the width of the portion 17 along the marking MK is same or substantially same as the width of the central portion 13. However, the width of the portion 17 may be smaller or greater than the width of the central portion 13 as long as the portion 17 is detachable. The holding portion 16 has a print 71A indicating the direction towards which the insulating tab 10A should be pulled. For example, the print 71A is printed on the upper cover layer 20 and/or the lower cover layer 60.

With this configuration, similarly to the insulating tab 10, the medical device 1 can be inspected using its battery power with the insulating tab 10A attached. Thereafter, the portion 17 including the electrodes 31 and 51 can be detached for delivery to the end user. Since the electrodes 31 and 51 no longer exist, the end user handles the insulating tab 10A as a known insulating pull tab and removes the insulating tab 10A before his or her initial use of the medical device 1.

FIG. 12 depicts an insulating tab 10B according to an embodiment. Unlike the insulating tabs 10 and 10A shown in FIGS. 7 and 11, the insulating tab 10B includes, at one end thereof, a portion 18 including the electrode 51 and a portion 19 including the electrode 31 and extending from the portion 18 along the longitudinal direction of the insulating tab 10B. Since the insulating tab 10B is thin and flexible, the portion 19 can be bent by hand such that the electrode 31 directly contacts the electrode 51. Thus, the conductive clip 80 is unnecessary to run the self-test for the medical device 1 using its own battery power.

In order to form the portions 18 and 19 of the insulating tab 10B, the electrodes 31 and 51 need to face the same direction, e.g., the upward direction from the upper cover layer 20. To form the structure, for example, each of the upper cover layer 20 and the base layer 40 has an opening to expose the electrode 51 therefrom. Instead, the lower cover layer 60 does not have any opening. Any other stacked structure may be used as long as the portion 19 of the insulating tab 10B is bendable by hand so that the electrode 31 can contact the electrode 51.

Additionally, one or more of the layers 20-60 have markings MK between the portions 18 and 19 such that the portion 19 including the electrode 31 is cut and detached along the markings MK. Thus, the medical device 1 is ready for delivery once the inspection is done and the portion 19 is detached from the insulating tab 10B.

With this configuration, the inspection of the medical device 1 can be done without any additional part like the conductive clip 80. Moreover, the electrode 31 is cut and detached along the markings MK after the inspection is done. After the removal of the portion 19, the end user treats the insulating tab 10B as a known insulating pull tab and starts the actual use of the medical device 1 after pulling the insulating tab 10B from the housing 101 of the medical device 1.

Figure 13:
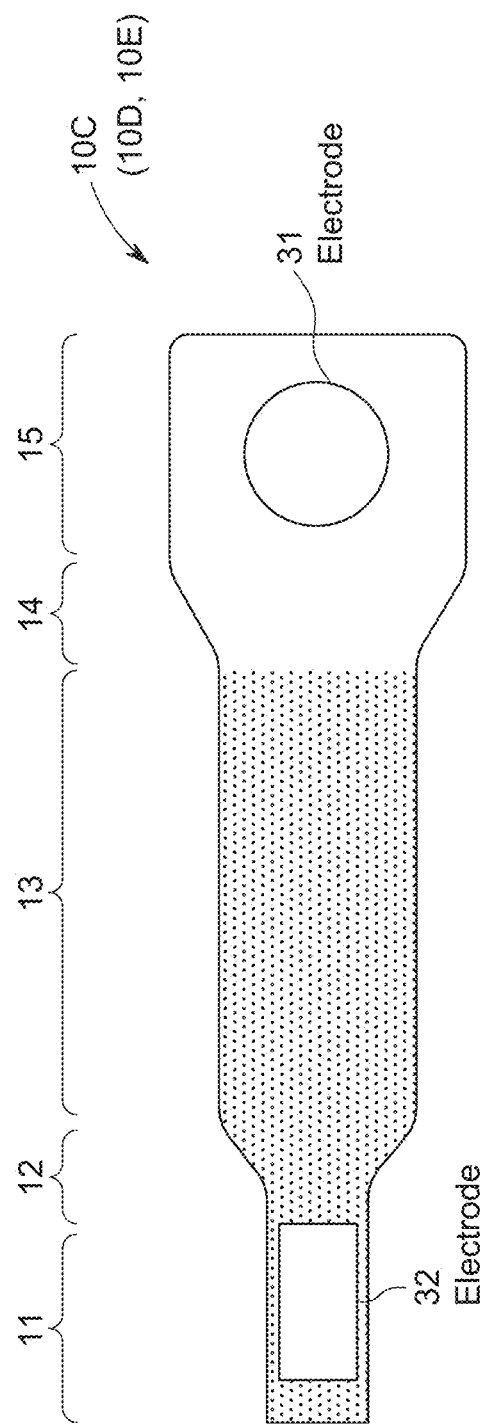

FIG. 13 depicts insulating tabs 10C, 10D, and 10E according to various embodiments.

The insulating tab 10C according to an embodiment has a similar shape to the insulating tab 10 as shown in FIG. 7. However, the insulating tab 10C is different in the upper and lower cover layers 20 and 60 corresponding to the narrow portion 11, the connecting portion 12, and the central portion 13, which have a higher lubricity than the other portions.

For example, a lubricant, such as a PTFE (polytetrafluoroethylene) coating, is applied to the surfaces of the upper and lower cover layers 20 and 60 corresponding to the narrow portion 11, the connecting portion 12, and the central portion 13. Alternatively, those surfaces are smoothed so as to have a higher lubricity than the other portions. According to the high lubricity, the insulating tab 10C can be easily removed from the housing 101 of the medical device 1.

In the example of FIG. 13, the surfaces of the upper and lower cover layers 20 and 60 corresponding to the narrow portion 11, the connecting portion 12, and the central portion 13 have a higher lubricity. Alternatively, the surfaces of the upper and lower cover layers 20 and 60 corresponding to one or more of the narrow portion 11, the connecting portion 12, the central portion 13, and the connection portion 14 may have a higher lubricity than the other portions.

The insulating tab 10D according to an embodiment has a similar shape to the insulating tab 10 as shown in FIG. 7. However, the insulating tab 10D is different in the narrow portion 11, the connecting portion 12, and the central portion 13, which have a higher tensile strength than the other portions.

For example, the upper and lower cover layers 20 and 60 corresponding to the narrow portion 11, the connecting portion 12, and the central portion 13 are made of a plastic material (e.g., PET) having a higher tensile strength per unit area than the one used in the other portions (e.g., PE). The higher tensile strength prevents the insulating tab 10D from being broken when it is pulled out from the housing 101 of the medical device 1.

In the example of FIG. 13, the narrow portion 11, the connecting portion 12, and the central portion 13 have a higher tensile strength than the other portions. Alternatively, one or more of the narrow portion 11, the connecting portion 12, the central portion 13, and the connection portion 14 may have a higher tensile strength than the other portions.

The insulating tab 10E according to an embodiment has a similar shape to the insulating tab 10 as shown in FIG. 7. However, the insulating tab 10E is different in the narrow portion 11, the connecting portion 12, and the central portion 13, which are thicker than the other portions.

For example, the upper and lower cover layers 20 and 60 corresponding to the narrow portion 11, the connecting portion 12, and the central portion 13 are thicker than the other portions. Alternatively, an additional layer may be added on or inserted between the upper and lower cover layers 20 and 60 corresponding to the narrow portion 11, the connecting portion 12, and the central portion 13. The higher thickness prevents the insulating tab 10E from being broken when it is pulled out from the housing 101 of the medical device 1.

In the example of FIG. 13, the narrow portion 11, the connecting portion 12, and the central portion 13 are thicker than the other portions. Alternatively, one or more of the narrow portion 11, the connecting portion 12, the central portion 13, and the connection portion 14 may be thicker than the other portions. In one embodiment, a label indicating the pull direction may be printed or attached to one or both of the surfaces of the thicker portions, e.g., the surface of the upper cover layer 20 corresponding to the central portion 13.

Figure 14:
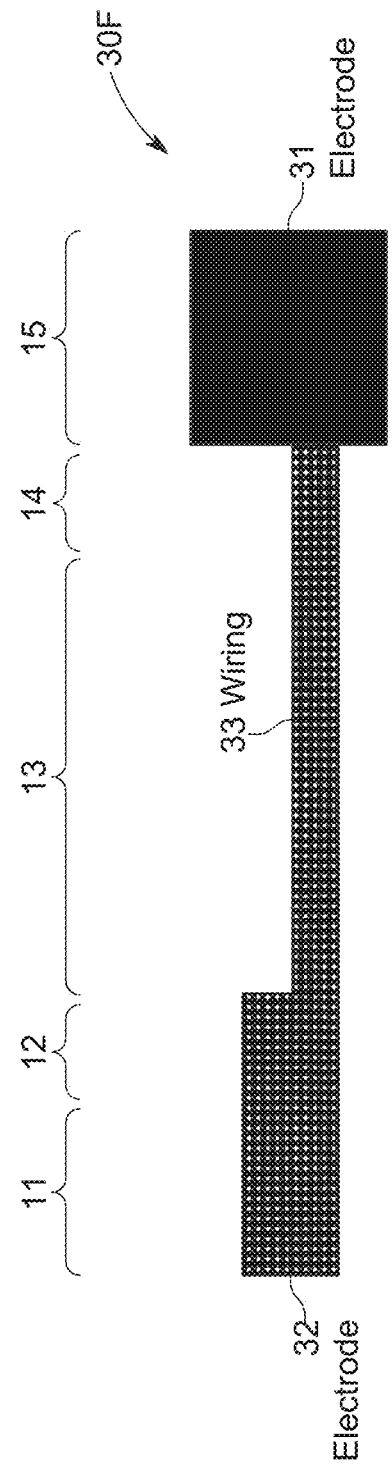

FIG. 14 depicts a conductive layer 30F in an insulating tab 10F according to an embodiment. The insulating tab 10F has a similar shape to the insulating tab 10 as shown in FIG. 7. However, the insulating tab 10F is different in the conductive layer 30F corresponding to the narrow portion 11, the connecting portion 12, and the central portion 13, which includes a higher amount of metal than the other portions. As a result, the insulating tab 10F is prevented from being broken when it is pulled out from the housing 101 of the medical device 1.

In the example of FIG. 14, the conductive layer 30F corresponding to the narrow portion 11, the connecting portion 12, and the central portion 13 contains a higher amount of metal than the other portions. Alternatively, the conductive layer 30F or 50F corresponding to one or more of the narrow portion 11, the connecting portion 12, the central portion 13, and the connection portion 14 may contain a higher amount of metal than the other portions.

Figure 15:
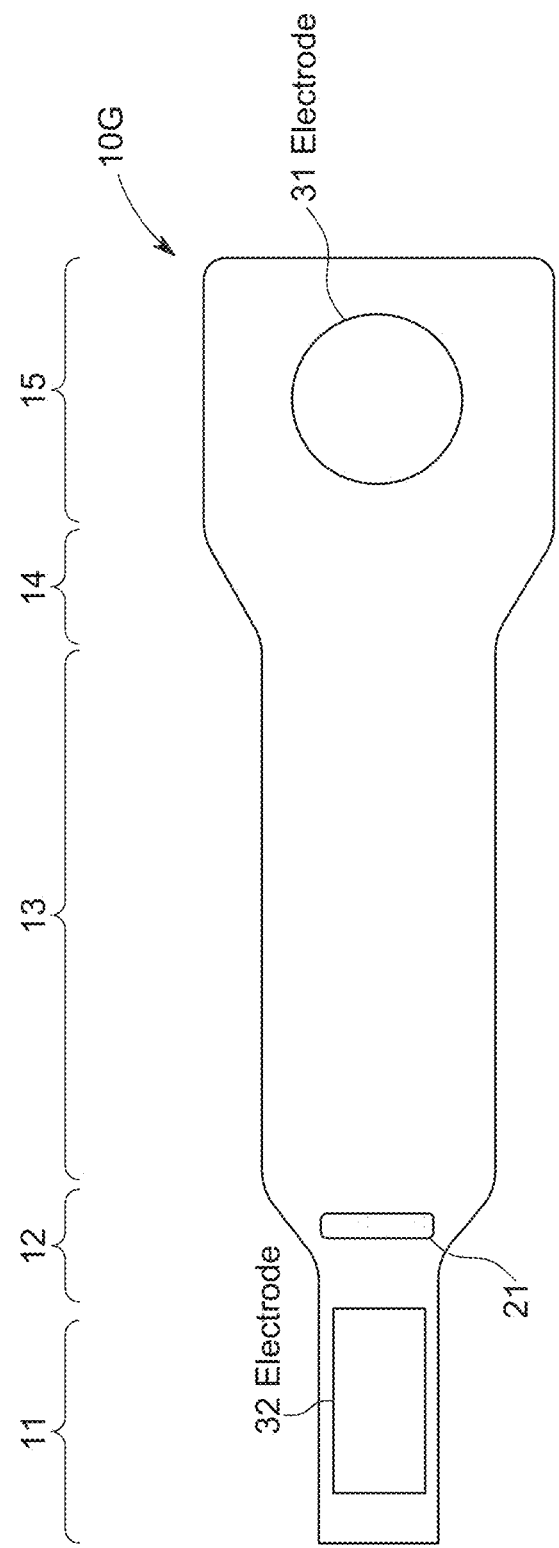

FIG. 15 depicts an insulating tab 10G according to an embodiment. The insulating tab 10G has a similar shape to the insulating tab 10 as shown in FIG. 7. The insulating tab 10G has a bumper 21 on the surface of the upper cover layer 20, which is designed to interfere with the battery holder 117. For example, the bumper 21 contacts the outside of the opening shown in FIG. 5. This will make placement of the insulating tab 10G easier by the manufacturer or assembler; the insulating tab 10G is slid into the battery holder 117 until it cannot go any further. The insulating tab 10G may have another bumper on the surface of the lower cover layer 60.

Figure 16:
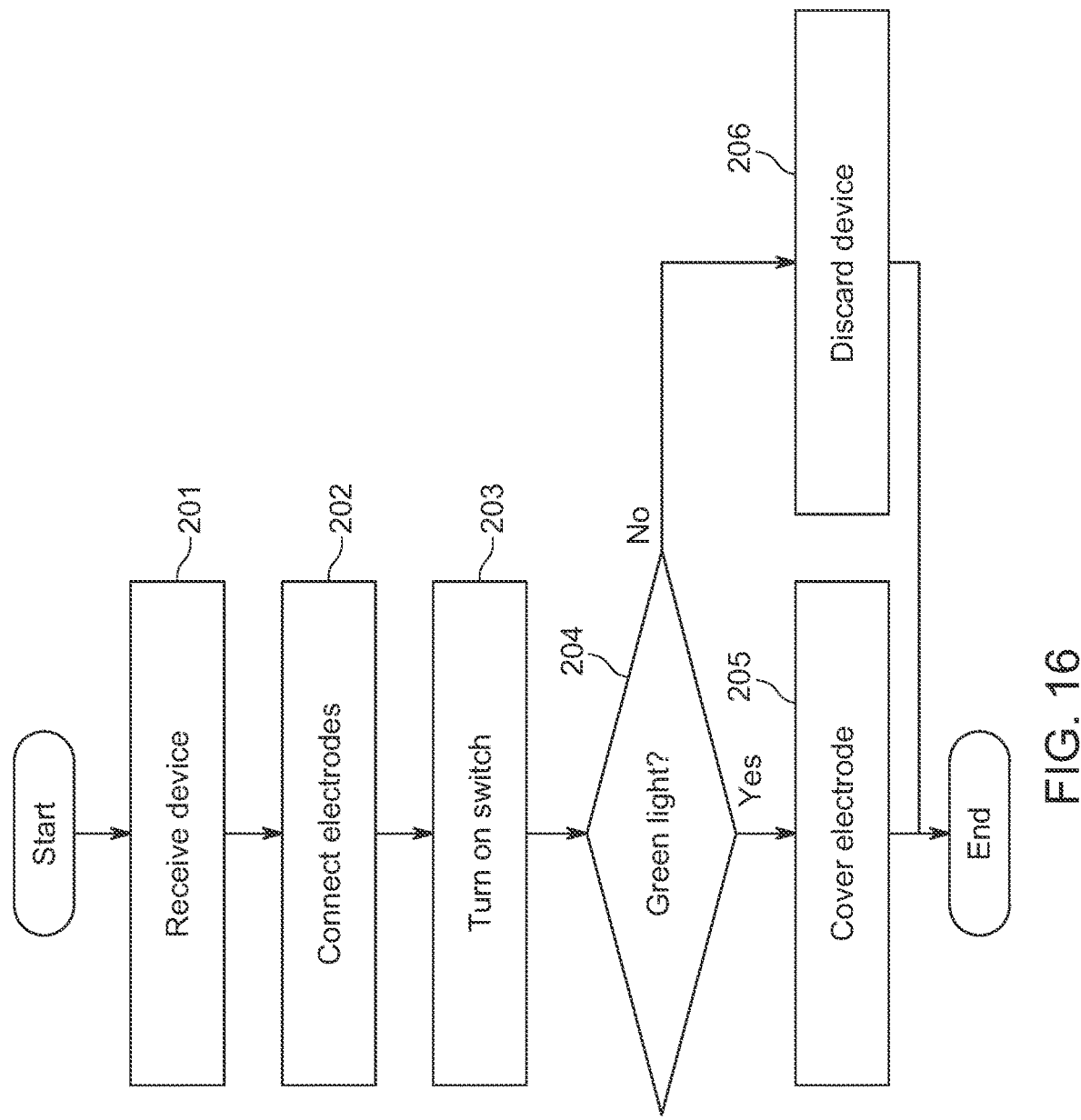
FIGS. 16 and 17 depict a method for inspecting a medical device according to one embodiment.
Figure 17:
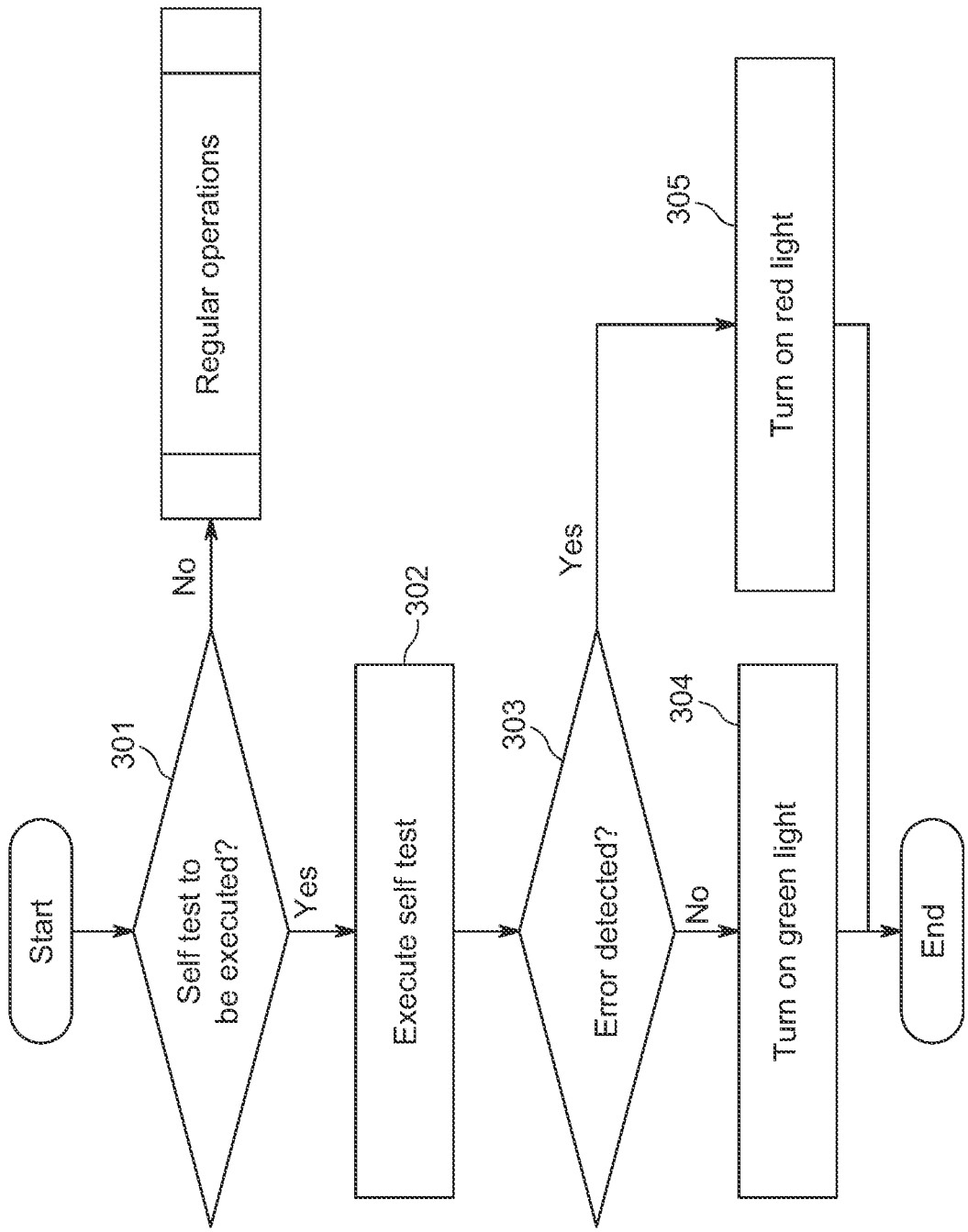

FIGS. 16 and 17 depict a method for inspecting the medical device 1 according to one embodiment. Specifically, FIG. 16 depicts the steps performed by the intervening party who receives the medical device 1 from the manufacturer and inspects it before delivery to the end user. In step 201, the intervening party receives the medical device 1 to which the insulating tab 10 is attached. Next, in step 202, the intervening party attaches the conductive clip 80 to the end of the insulating tab 10 so that the electrodes 31 and 51 are electrically connected. Then, in step 203, the intervening party turns on the switch 102 of the medical device 1.

FIG. 17 depicts the steps performed by the electrical circuit 141 of the medical device 1 when the power is on, i.e., the switch 102 is turned on after the electrodes 31 and 51 of the insulating tab 10 are electrically connected or the insulating tab 10 is removed. After the medical device 1 is turned on, in step 301, the electrical circuit 141 determines whether to execute the self-test. The self-test is designed to check that the circuit is connected and functioning. The restored power to the medical device 1 also allows for other functional tests to be performed at this time to determine whether the functions of each electrical component (e.g., the motor 121, the batteries 111, and/or the electrical circuit 141 itself) work correctly. Typically, the self-test is executed once before delivery to the end user. For example, the electrical circuit 141 refers to a flag stored in an embedded non-volatile memory and determines to perform the self-test if the flag is enabled. The electrical circuit 141 disables the flag once the initial self-test is done. When the flag is disabled upon startup, the electrical circuit 141 proceed with the regular operations of the medial device 1.

After the electrical circuit 141 executes the self-test in step 302, when no error is detected, the electrical circuit 141 controls the light elements 103 to emit green light in step 304. Otherwise, the electrical circuit 141 controls the light elements 103 to emit red light in step 305.

Referring back to FIG. 16, in step 204, the intervening party checks whether green light is emitted from the light elements 103. When green light is emitted, in step 205, the intervening party removes the conductive clip 80 from the insulating tab 10 and attaches the sticker 70 thereto such that the electrodes 31 and 51 are covered. The medical device 1 with the insulating tab 10 to which the sticker 70 is attached is then delivered to the end user. On the other hand, when green light is not emitted, in step 206, the intervening party discards or reworks the medial device 1.

The above-described inspection methods are modified when the inspection tabs 10A and 10B shown in FIGS. 11 and 12 are used. Specifically, when the insulating tab 10A or 10B is used, in step 205, the intervening party detaches the portion 17 including the electrodes 31 and 51 or the portion 19 including the electrode 31 instead of attaching the sticker 70 thereto. Additionally, when the insulating tab 10B is used, in step 202, the intervening party bends the insulating tab 10B so that the electrode 31 contacts the electrode 51 instead of attaching the conductive clip 80 thereto.

According to the aforementioned embodiments, the medical device 1 can execute the self-test using its own battery power with the insulating tab 10-10G attached thereto. The internal circuit can be completed by the conductive clip 80 attached to the electrodes 31 and 51 that are outside the housing 101 of the medical device 1. After the self-test, one or both of the electrodes 31 and 51 can be covered by the sticker 70 or removed. As a result, the pre-shipment inspection can be conducted by the intervening party without reassembling of the medical device 1 or external power supply. Moreover, since the outside electrodes 31 and/or 51 of the insulating tab 10-10G are invisible to the end user, he or she can treat the insulating tab 10 as a common battery insulating pull tab and simply pull out the insulating tab 10-10G prior to the use of the medical device 1.

In this disclosure, various embodiments are described separately. However, each embodiment can be combined with one or more of the other embodiments. For example, the portions 11-13 of the insulation tab 10A shown in FIG. 11 may have a higher lubricity or a higher tensile strength than the other portions 16 and 17 (see FIG. 13). Further, the bump 21 shown in FIG. 15 may be applied to any embodiment described above.

In the above description, the medical device 1 is explained as an electronic device to which the insulating tab 10 is attached. However, the above-described embodiments can apply to any other battery-driven device, such as consumer electronic devices, that requires the temporary use of its embedded battery for inspection.

What is claimed is:

1. An insulating tab attachable to an electronic device driven by a battery, comprising:
    first, second, and third insulating layers that extend along a first direction, the first insulating layer being between the second and third insulating layers, a surface area of each of the second and third insulating layers being smaller than a surface area of the first insulating layer;
    a first wiring that extends along the first direction on a first surface of the first insulating layer, the first wiring including a first electrode on one end thereof and a second electrode on the other end thereof, the first electrode being exposed at a first location of the first insulating layer at which the first insulating layer and each of the second and third insulating layers do not overlap each other; and
    a second wiring that extends along the first direction on a second surface of the first insulating layer that is opposite to the first surface, the second wiring including a third electrode on one end thereof and a fourth electrode on the other end thereof, the third electrode being exposed at the first location of the first insulating layer.

2. The insulating tab according to claim 1, wherein the first and third electrodes are exposed at the first location of the first insulating layer through respective first openings in the second and third insulating layers.

3. The insulating tab according to claim 2, wherein at least one of the second and third insulating layers has a bumper adjacent to the first opening.

4. The insulating tab according to claim 1, wherein the second and fourth electrodes are exposed at a second location of the first insulating layer at which the first insulating layer and each of the second and third insulating layers do not overlap each other.

5. The insulating tab according to claim 1, wherein the second and third insulating layers have substantially the same outer shape.

6. The insulating tab according to claim 5, wherein
    the second insulating layer has first and second end portions at opposite ends thereof in the first direction, and
    a first width of the first end portion is smaller than a second width of the second end portion.

7. The insulating tab according to claim 6, wherein a third width of a middle portion of the second insulating layer, which is between the first and second end portions, is larger than the first width and smaller than the second width.

8. The insulating tab according to claim 7, wherein a first length of the first end portion and a second length of the second end portion are each less than a third length of the middle portion.

9. The insulating tab according to claim 5, wherein at least one of the first insulating layer, the first wiring, the second insulating layer, the second wiring, and the third insulating layer includes markings at a location along the first direction between a widest portion of the insulating tab and a location of the second and fourth electrodes.

10. The insulating tab according to claim 5, wherein
    the first insulating layer, the first wiring, the second insulating layer, the second wiring, and the third insulating layer are deformable,
    the first wiring extends along the first direction further than the second wiring, and
    a portion of the first wiring including the second electrode is detachable.

11. The insulating tab according to claim 1, wherein at least one of the second and third insulating layers includes a portion having a higher lubricity than the other portion thereof.

12. The insulating tab according to claim 1, wherein the first insulating layer includes a portion having a higher tensile strength than the other portion thereof.

13. The insulating tab according to claim 1, wherein the first insulating layer includes a portion that is thicker than the other portion thereof.

14. The insulating tab according to claim 1, wherein at least one of the first and second wirings includes a portion including a higher amount of metal than the other portion thereof.

15. An insulating tab, comprising:
    a first portion including first and second electrodes facing away and insulated from each other by a first insulating layer and insertable into an electronic device;
    a second portion including third and fourth electrodes insulated from each other by the first insulating layer and located outside when the first portion is inserted into the electronic device; and
    a third portion between the first and second portions and including a first wiring that connects the first and third electrodes and a second wiring that connects the second and fourth electrodes, the first and second wirings being insulated from each other by the first insulating layer and respectively covered by second and third insulating layers between which the first insulating layer extends, wherein
    the first and third electrodes are exposed towards a first direction and the second and fourth electrodes are exposed towards a second direction that is opposite to the first direction.

16. The insulating tab according to claim 15, wherein
    a width of the first portion is smaller than a width of the third portion, and
    a width of the second portion is greater than the width of the third portion.

17. An electronic device, comprising:
    a housing;
    one or more batteries stored in the housing;
    an electrical circuit;
    a plurality of device electrodes electrically connecting the batteries and the electrical circuit; and
    a detachable insulating tab including:

first, second, and third insulating layers that extend along a first direction, the first insulating layer being between the second and third insulating layers, a surface area of each of the second and third insulating layers being smaller than a surface area of the first insulating layer, a first wiring that extends along the first direction on a first surface of the first insulating layer, the first wiring including a first electrode on one end thereof and a second electrode on the other end thereof, the first electrode being exposed at a first location of the first insulating layer at which the first insulating layer and each of the second and third insulating layers do not overlap each other, and a second wiring that extends along the first direction on a second surface of the first insulating layer that is opposite to the first surface, the second wiring including a third electrode on one end thereof and a fourth electrode on the other end thereof, the third electrode being exposed at the first location of the first insulating layer, wherein the first electrode contacts one of the device electrodes and the third electrode contacts a terminal of one of the batteries, or the first and third electrodes contact terminals of two of the batteries that are connected in series, and the second and fourth electrodes are outside the housing.

18. An inspection method using the electronic device of claim 17, the method comprising:
   acquiring the electronic device for inspection;
   electrically connecting the second and fourth electrodes to cause the electrical circuit to perform a self-test; and
   determining success or failure of the self-test.

19. The inspection method according to claim 18, further comprising:

placing a sticker formed of a non-conductive material on the second and fourth electrodes after the determination.

20. An insulating tab insertable between terminals of an electronic device for preventing power from being supplied by a battery of the electronic device, comprising:
   a first insulating layer that extends along a first direction;
   a first wiring on a first surface of the first insulating layer, the first wiring including a first electrode on one end thereof and a second electrode on the other end thereof; and
   a second wiring on a second surface of the first insulating layer that is opposite to the first surface, the second wiring including a third electrode on one end thereof and a fourth electrode on the other end thereof, wherein
   the first and third electrodes are disposed on opposite sides of the first insulating layer at a first location of the first insulating layer,
   the second and fourth electrodes are disposed on opposite sides of the first insulating layer at a second location of the first insulating layer, and
   the insulating tub further comprises:
      a second insulating layer that partially covers the first wiring such that the first and second electrodes are exposed towards a second direction perpendicular to the first direction, and
      a third insulating layer that partially covers the second wiring such that the third and fourth electrodes are exposed towards a third direction that is opposite to the second direction.

21. The insulating tab according to claim 20, wherein a surface area of each of the second and third insulating layers is smaller than a surface area of the first insulating layer.

* * * * *